(12) United States Patent
Porretta et al.

(10) Patent No.: US 8,750,694 B1
(45) Date of Patent: Jun. 10, 2014

(54) AUTOMOBILE 12 VOLT AIR FRESHENER

(76) Inventors: Doreen Porretta, Locust Valley, NY (US); Antoinette Porretta, Locust Valley, NY (US)

( * ) Notice: Subject to any disclaimer, the term of this patent is extended or adjusted under 35 U.S.C. 154(b) by 445 days.

(21) Appl. No.: 13/300,310

(22) Filed: Nov. 18, 2011

(51) Int. Cl.
*F24F 6/08* (2006.01)

(52) U.S. Cl.
USPC ............ 392/395; 392/386; 392/394; 392/390

(58) Field of Classification Search
None
See application file for complete search history.

(56) References Cited

U.S. PATENT DOCUMENTS

| | | | |
|---|---|---|---|
| 4,968,456 A | 11/1990 | Muderlak et al. | |
| 5,373,581 A * | 12/1994 | Smith | 392/390 |
| 5,394,506 A * | 2/1995 | Stein et al. | 392/395 |
| 5,788,931 A | 8/1998 | Munoz | |
| 6,021,254 A * | 2/2000 | Hunter | 392/390 |
| 6,592,828 B2 | 7/2003 | Munoz | |
| D486,213 S * | 2/2004 | Novak | D23/366 |
| D532,892 S * | 11/2006 | Koon | D23/366 |
| 8,197,761 B1 * | 6/2012 | Miller-Larry | 422/125 |
| D692,550 S * | 10/2013 | Wirz | D23/366 |
| 2002/0176704 A1 | 11/2002 | Roe | |

* cited by examiner

*Primary Examiner* — Thor Campbell
(74) *Attorney, Agent, or Firm* — Crossley Patent Law; Micah C. Gunn

(57) ABSTRACT

An automobile 12 volt air freshener that includes a connecter portion and a head portion, the connecter portion interconnectable with an automobile cigarette lighter, the head portion rotatably, anglably, and extensibly moveable upon a shaft disposed on a proximal end of the connector portion, the head portion including a bulb-shaped casing and an interior cavity, the head portion having a thermostat disposed within the interior cavity, the thermostat in operational communication with a heating element, with a fill reservoir releasably attachable to a reservoir input by means of a threaded fastener, whereby an aromatic scent disposed within the fill reservoir is conveyed to a sorbent member within the interior cavity, and the aromatic scent is volitalized when the heating element is activated.

12 Claims, 4 Drawing Sheets

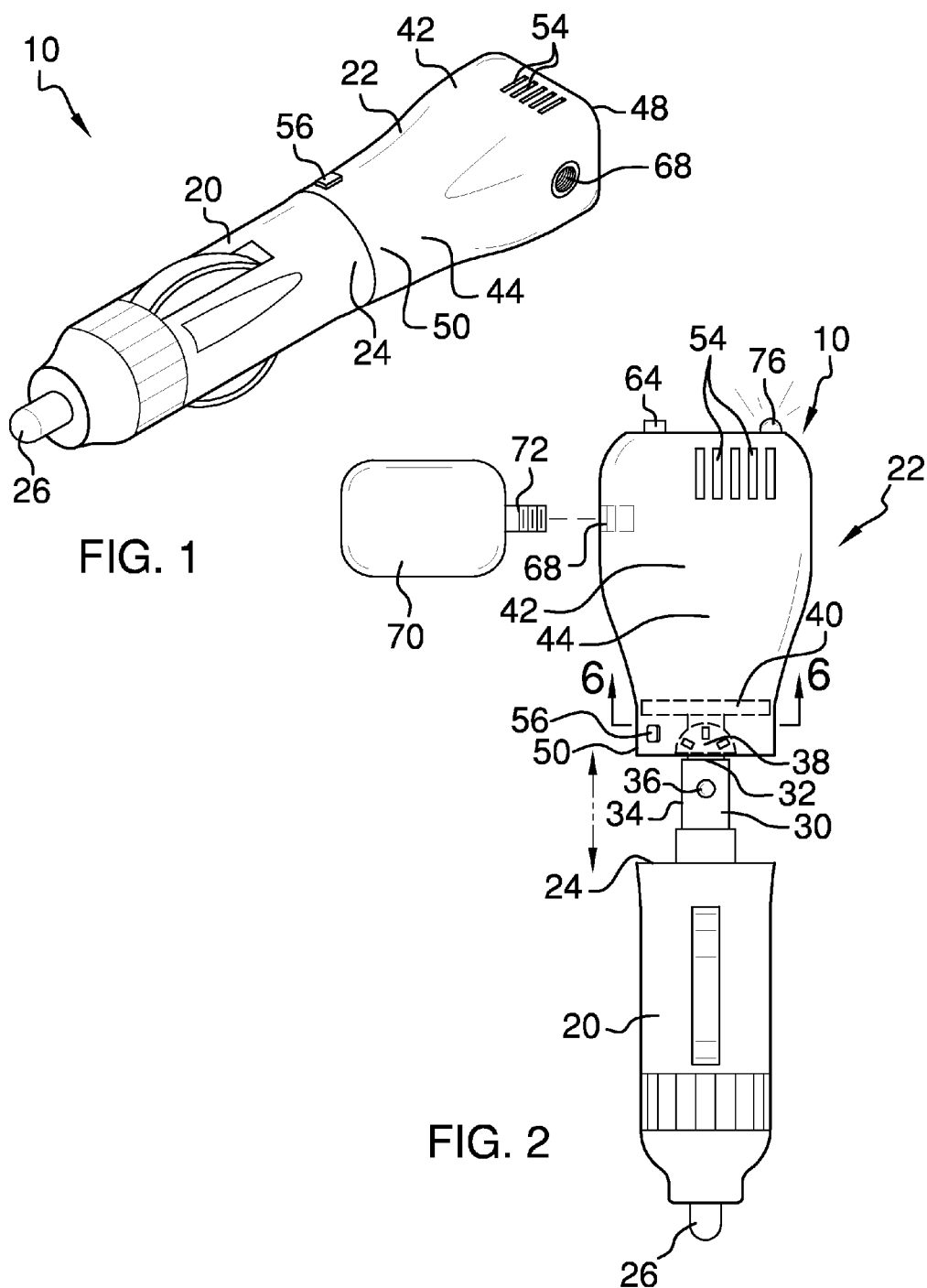

AUTOMOBILE 12 VOLT AIR FRESHENER

BACKGROUND OF THE INVENTION

Various types of automobile 12 volt air fresheners are known in the prior art. However, what is needed is an automobile 12 volt air freshener that includes a connecter portion and a head portion, the connecter portion interconnectable with an automobile cigarette lighter, the head portion rotatably, anglably, and extensibly moveable upon a shaft disposed on a proximal end of the connector portion, the head portion including a bulb-shaped casing and an interior cavity, the head portion having a thermostat disposed within the interior cavity, the thermostat in operational communication with a heating element, with a fill reservoir releasably attachable to a reservoir input by means of a threaded fastener, whereby an aromatic scent disposed within the fill reservoir is conveyed to a sorbent member within the interior cavity, and the aromatic scent is volitalized when the heating element is activated.

FIELD OF THE INVENTION

The present invention relates to an automobile 12 volt air freshener, and more particularly, to an automobile 12 volt air freshener that includes a connecter portion and a head portion, the connecter portion interconnectable with an automobile cigarette lighter, the head portion rotatably, anglably, and extensibly moveable upon a shaft disposed on a proximal end of the connector portion, the head portion including a bulb-shaped casing and an interior cavity, the head portion having a thermostat disposed within the interior cavity, the thermostat in operational communication with a heating element, with a fill reservoir releasably attachable to a reservoir input by means of a threaded fastener, whereby an aromatic scent disposed within the fill reservoir is conveyed to a sorbent member within the interior cavity, and the aromatic scent is volitalized when the heating element is activated.

SUMMARY OF THE INVENTION

The general purpose of the automobile 12 volt air freshener, described subsequently in greater detail, is to provide an automobile 12 volt air freshener which has many novel features that result in an automobile 12 volt air freshener which is not anticipated, rendered obvious, suggested, or even implied by prior art, either alone or in combination thereof.

The present automobile 12 volt air freshener includes a connector portion and a head portion. The connector portion is configured to releasably engage with an automobile 12 volt cigarette lighter and includes a distal end and a proximal end. A shaft is centrally disposed on the proximal end. The shaft includes a central portion and an outmost end. A tilt mechanism is disposed on the outmost end and a disk member is vertically oriented and centrally disposed on the outmost end.

The head portion includes a generally bulb-shaped casing having a neck portion, an external surface, and a generally rectangular proximal side. An interior cavity is disposed within the head portion. A plurality of vents are disposed on the external surface of the bulb-shaped casing and the proximal side. A switch is disposed on the external surface of the proximal side and an LED indicator is disposed on the external surface of the proximal side. A tilt button is disposed on the external surface of the neck portion.

The head portion is disposed upon the shaft outmost end, the disk member disposed within a rotatable ring disposed in the neck portion. The rotatable ring rotatably moves circumferentially round the disk member, positioning the head portion through 360 degrees relative the shaft. The tilt mechanism releasably positions the head portion in a coronal plane relative the tilt mechanism, the head portion releasably moveable between an aligned position, a left position, and a right position. The tilt mechanism is in operational communication with the tilt button; when the tilt button is depressed the head portion is moveable between the aligned position, the left position, and the right position. The head portion is releasably lockable in said aligned position, left position, and right position, and the tilt button resets when the head portion is moved to the aligned position, the left position, and the right position.

A heating element is disposed within the interior cavity. A thermostat, in operational communication with the heating element, is disposed within the interior cavity. A plurality of wiring interconnects the heating element, the thermostat, the switch, the LED, and the connecter portion distal end in circuit. The switch is moveable between a first position, a second position, and a third position. When the switch is moved to the first position, the heating element is activated, the heating element controlled by the thermostat to a first temperature. When the switch is moved to the third position, the heating element is activated, the heating element controlled by the thermostat to a second temperature. When the switch is moved to the first position the heating element is deactivated.

The LED illuminates when the switch is moved to the second position and the third position. The LED is deactivated with the switch is in the first position.

A sorbent component is disposed within the interior cavity. The sorbent component is configured to sorb an aromatic scent. A reservoir input is disposed through the external surface, the reservoir input interconnected to the sorbent component. A disposable fill reservoir releasably interconnects with the reservoir input by means of a threaded fastener, and an aromatic scent is drawn to the sorbent component through the reservoir input. When the heating element is activated, the aromatic scent is volatilized, the scent dispersed through the plurality of vents into the interior of an automobile wherein the device is used.

Alternate aromatic scents are envisioned to be available for use with the device, as agreeable to the particular tastes of individuals using the device.

Thus has been broadly outlined the more important features of the present automobile 12 volt air freshener so that the detailed description thereof that follows may be better understood and in order that the present contribution to the art may be better appreciated.

Objects of the present automobile 12 volt air freshener, along with various novel features that characterize the invention are particularly pointed out in the claims forming a part of this disclosure. For better understanding of the automobile 12 volt air freshener, its operating advantages and specific objects attained by its uses, refer to the accompanying drawings and description.

BRIEF DESCRIPTION OF THE DRAWINGS

Figures

FIG. 1 is an isometric view.

FIG. 2 is a top view.

DETAILED DESCRIPTION OF THE DRAWINGS

Figure 2A:
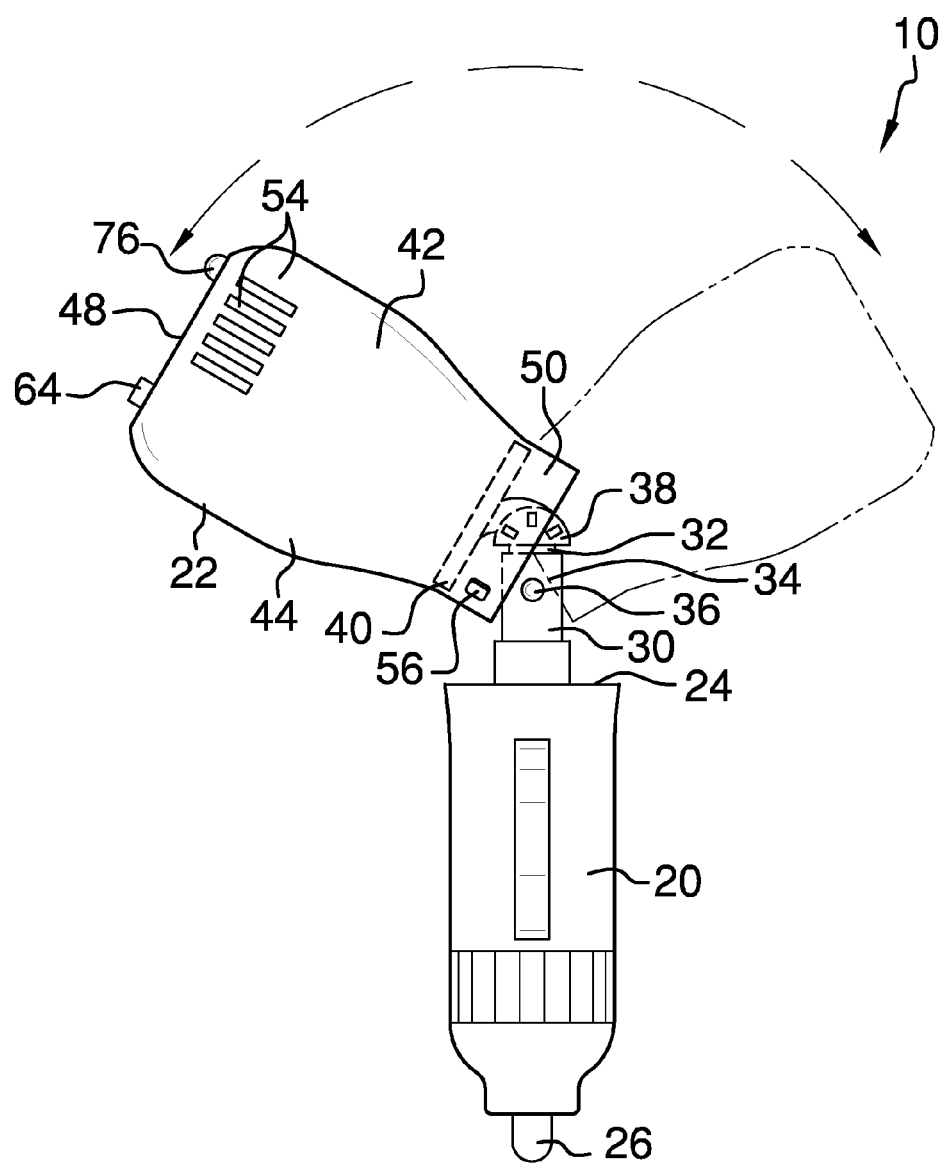
FIG. 2A is a top view illustrating the movement of a tilt mechanism.
Figure 3:
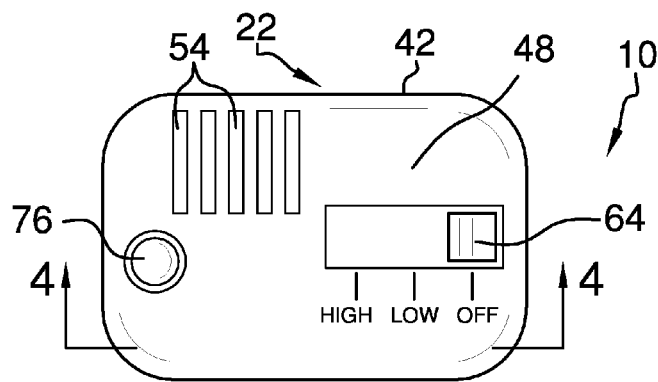
FIG. 3 is a front view.
Figure 6:
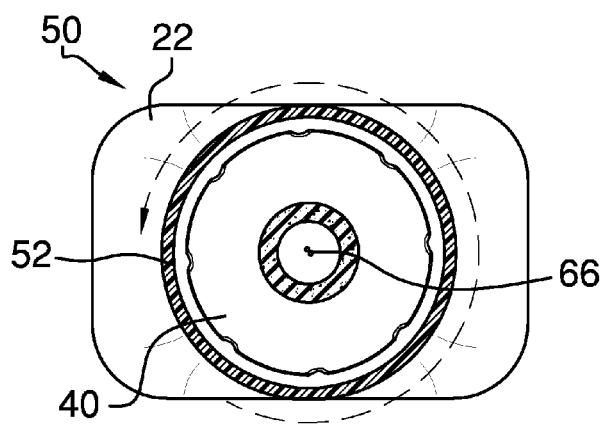
FIG. 6 is a cross-section view taken along the line 6-6 of FIG. 2.
Figure 4:
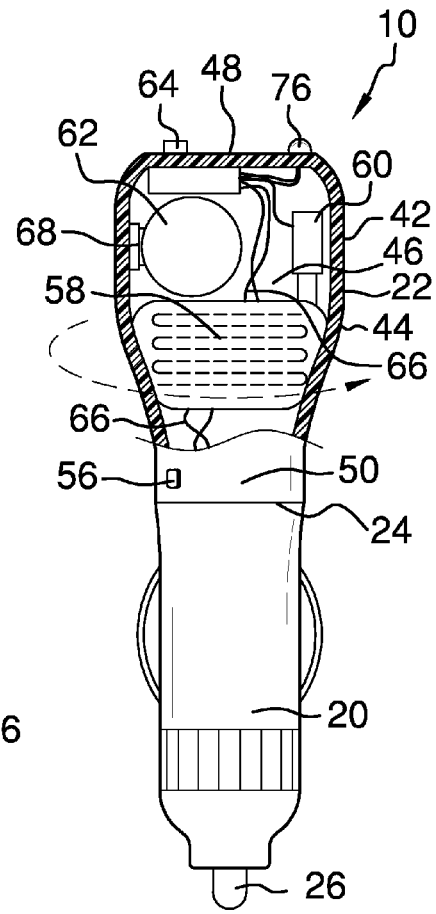
FIG. 4 is a cross-section view taken along the line 4-4 of FIG. 3.
Figure 5:
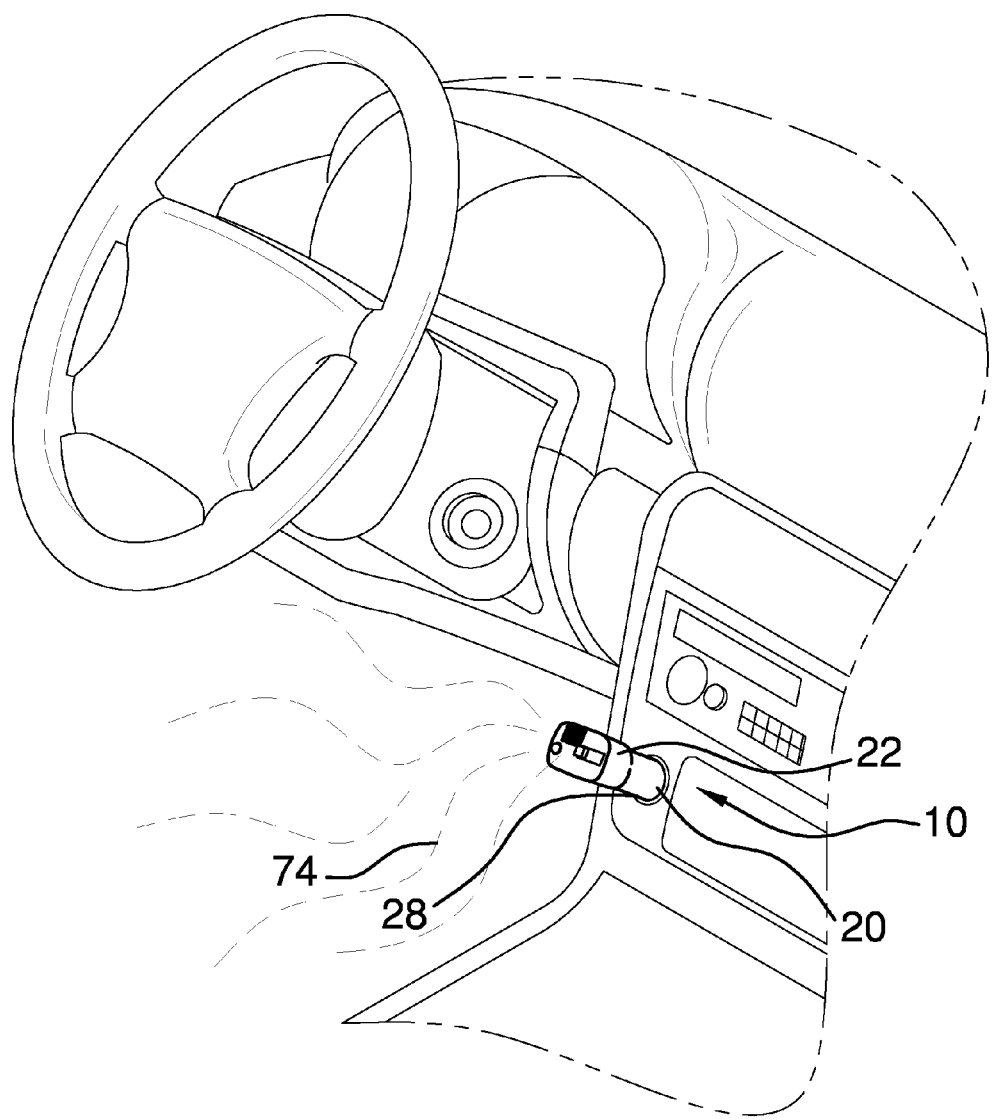
FIG. 5 is an in-use view.

With reference now to the drawings, and in particular FIGS. 1 through 6 thereof, example of the instant automobile 12 volt air freshener employing the principles and concepts of the present automobile 12 volt air freshener and generally designated by the reference number 10 will be described.

Referring to FIGS. 1 through 6 a preferred embodiment of the present automobile 12 volt air freshener 10 is illustrated.

The automobile 12 volt air freshener 10 includes a connector portion 20 and a head portion 22. The connector portion 20 has a proximal end 24 and a distal end 26. The connecter portion 20 is configured to interconnect with an automobile 12 volt cigarette lighter outlet 28 at the distal end 26.

A shaft 30 is centrally disposed on the connecter portion 20 proximal end 24. The shaft 30 includes an outmost end 32, a central portion 34, a ball detent 36 disposed on the central portion 34, a tilt mechanism 38 disposed on the outmost end 32, and a vertically oriented disk member 40 transversely disposed on the tilt mechanism 38.

The head portion 22 is extensibly disposed on the shaft 30. The head portion 22 includes a generally bulb-shaped casing 42. The casing 42 includes an external surface 44, an interior cavity 46, a generally rectangular proximal surface 48, and a neck portion 50. A rotatable ring 52 is disposed in the interior cavity 46 of the neck portion 50, the rotatable ring 52 rotatably moveable around the disk member 40. The rotatable ring 52 releasably engages with the disk member 40 at a plurality of positions rotatable though 360 degrees and the head portion 22 rotates through 360 degrees by means of the rotatable ring 52 releasably engaging with the disk member 40. A plurality of vents 54 is disposed on the external surface 44. A tilt button 56 is disposed on the external surface 44, the tilt button 56 releasably engaging the tilt mechanism 38 when depressed.

The head portion 22 moves between a first position and an extended position (see FIG. 2) along the shaft 30. The ball detent 36 releasably engages the head portion 22 around the shaft 30 in the first position. The head portion 22 is released from the first position when the tilt button 56 is depressed. The tilt mechanism 38 enables the head portion 22 to move in a coronal plane relative the tilt mechanism 38 (see FIG. 2A). The tilt mechanism 38 enables motion of the head portion 22 between an aligned position, a left position and a right position.

The tilt button 56 releasably engages the head portion in the aligned position, the left position, and the right position. When the tilt button 56 is depressed, the head portion 22 is moveable between the aligned position, the left position, and the right position. The tilt button 56 resets when the head portion 22 is moved to the aligned position, the left position, and the right position.

A heating element 58 is disposed in the interior cavity 46. A thermostat 60 is disposed in the interior cavity 46, the thermostat 60 in operational communication with the heating element 58. A sorbent component 62 is disposed within the interior cavity 46. A switch 64 is disposed exteriorly on the proximal surface 48. A plurality of wiring 66 interconnects the switch 64, the thermostat 60, the heating element 58, and the connecter portion 20 distal end 26 in circuit.

The switch 64 is moveable between a first position, a second position, and a third position. The first position disables the heating element 58, the second position activates the heating element 58 to a first temperature, and the third position activates the heating element 58 to a second temperature. The heating element 58 first temperature and the heating element 58 second temperature are controlled and regulated by the thermostat 60.

A reservoir input 68 is disposed on the external surface 44, the reservoir input 68 interconnected to the sorbent component 62. A disposable fill reservoir 70 is releasably secureable to the reservoir input 68. The fill reservoir 70 releasably interconnects with the reservoir input 68 by means of a threaded fastener 72 disposed upon the fill reservoir 70. Aromatic scent 74 is sorbed into the sorbent component 62 through in the reservoir input 68. When the heating element 58 is activated, the aromatic scent 74 is volatilized from the sorbent component 62 to evanesce within the automobile interior.

A Light Emitting Diode 76 is disposed on the casing 42 external surface 44, the Light Emitting Diode 76 in circuit with the switch 64. The Light Emitting Diode 76 activates when the switch 64 is moved to the second position and alternately the third position to signal to a user the device 10 is activated.

Therefore, an aromatic scent is transferred to the sorbent component 62 by means of the fill reservoir 70 interconnecting with the sorbent component 62 by means of the reservoir input 68, the head portion 22 is extendible along the shaft 30, rotatable around the disk member 40, and moveable by means of the tilt mechanism 38; and the thermostat 60 regulates a temperature range to volatilize and disperse the aromatic scent 74 into the interior of an automobile, as desired.

What is claimed is:

1. An automobile 12 volt air freshener comprising:
   a connector portion configured to releasably interconnect with an automobile 12 volt cigarette lighter outlet, the connector portion having a proximal end and a distal end;
   a shaft centrally disposed on the connecter portion proximal end, the shaft comprising:
     an outmost end;
     a central portion;
     a ball detent disposed on the central portion;
     a tilt mechanism disposed on the shaft outmost end;
     a vertically oriented disk member centrally disposed on the tilt mechanism;
   a head portion extensibly disposed on the shaft, the head portion comprising:
     a generally bulb-shaped casing, the casing comprising:
       an external surface;
       an interior cavity;
       a generally rectangular proximal surface;
       a neck portion;
       a rotatable ring disposed in the interior cavity of the neck portion, the rotatable ring rotatably moveable around the disk member;
     a heating element disposed in the interior cavity;
     a thermostat disposed in the interior cavity;
     a sorbent component disposed within the interior cavity;
     a switch disposed on the proximal end external surface;
     a plurality of wiring interconnecting the switch, the thermostat, the heating coils, and the connecter portion distal end in circuit;
     a reservoir input disposed on the external surface, the reservoir input interconnected to the sorbent component;
     a tilt buttom disposed on the external surface, the tilt button releasably engaging the tilt mechanism;
     a plurality of vents disposed on the external surface;

a disposable fill reservoir releasably secureable to the reservoir input;

wherein an aromatic scent is transferred to the sorbent component by means of the fill reservoir interconnecting with the sorbent component by means of the reservoir input; the head portion is extendible along the shaft, rotatable around the disk member, and moveable by means of the tilt mechanism; and the thermostat regulates a temperature to disperse the aromatic scent into the interior of an automobile.

2. The automobile 12 volt air freshener of claim 1 wherein the switch is moveable between a first position, a second position, and a third position, wherein the first position disables the heating element, the second position activates the heating element to a first temperature, and the third position activates the heating element to a second temperature.

3. The automobile 12 volt air freshener of claim 2 wherein the heating element first temperature and the heating element second temperature are controlled and regulated by the thermostat.

4. The automobile 12 volt air freshener of claim 3 wherein the head portion moves between a first position and an extended position along the shaft.

5. The automobile 12 volt air freshener of claim 4 wherein the ball detent releasably engages the head portion around the shaft in the first position.

6. The automobile 12 volt air freshener of claim 5 wherein the head portion is released from the first position when the tilt button is depressed.

7. The automobile 12 volt air freshener of claim 6 wherein the tilt mechanism is moveable in a coronal plane relative the tilt mechanism and the head portion is thereby positional between an aligned position, a left position, and a right position.

8. The automobile 12 volt air freshener of claim 7 wherein the tilt button releasably engages the tilt mechanism to move between the aligned position, the left position, and the right position, when the tilt button is depressed, the tilt button resetting when the head portion is moved to the aligned position, the left position, and the right position.

9. The automobile 12 volt air freshener of claim 8 wherein the rotatable ring releasably engages with the disk member at a plurality of positions though 360 degrees.

10. The automobile 12 volt air freshener of claim 9 further comprising a Light Emitting Diode on the external surface, the Light Emitting Diode in circuit with the switch, the Light Emitting Diode activating when the switch is moved to the second position and alternately the third position.

11. The automobile 12 volt air freshener of claim 10 wherein the fill reservoir releasably interconnects with the reservoir input by means of a threaded fastener disposed upon the fill reservoir.

12. An automobile 12 volt air freshener comprising:
a connector portion configured to releasably interconnect with an automobile 12 volt cigarette lighter outlet, the connector portion having a proximal end and a distal end;
a shaft centrally disposed on the connecter portion proximal end, the shaft comprising:
an outmost end;
a central portion;
a ball detent disposed on the central portion;
a tilt mechanism disposed on the shaft outmost end;
a vertically oriented disk member centrally disposed on the tilt mechanism;
a head portion extensibly disposed on the shaft, the head portion comprising:
a generally bulb-shaped casing, the casing comprising:
an external surface;
an interior cavity;
a generally rectangular proximal surface;
a neck portion;
a rotatable ring disposed in the interior cavity of the neck portion, the rotatable ring rotatably moveable around the disk member;
a heating element disposed in the interior cavity;
a thermostat disposed in the interior cavity;
a sorbent component disposed within the interior cavity;
a switch disposed on the proximal end external surface;
a Light Emitting Diode disposed on the external surface;
a plurality of wiring interconnecting the switch, the Light emitting Diode, the thermostat, the heating coils, and the connecter portion distal end in circuit;
a reservoir input disposed on the external surface, the reservoir input interconnected to the sorbent component;
a tilt buttom disposed on the external surface, the tilt button releasably engaging the tilt mechanism;
a plurality of vents disposed on the external surface;
a disposable fill reservoir releasably secureable to the reservoir input;
a threaded fastener disposed on the fill reservoir, the threaded fastener releasably connectable to the reservoir input;
wherein an aromatic scent is transferred to the sorbent component by means of the fill reservoir interconnecting with the sorbent component by means of the reservoir input; the head portion is extendible along the shaft, rotatable around the disk member, and moveable by means of the tilt mechanism; and the thermostat regulates a temperature to disperse the aromatic scent into the interior of an automobile.

\* \* \* \* \*